(12) United States Patent
Toyota

(10) Patent No.: US 10,874,344 B2
(45) Date of Patent: *Dec. 29, 2020

(54) DEVICE FOR MEASURING ORAL CAVITY PRESSURE, PRESSURE MEASURING PROBE

(75) Inventor: Koichiro Toyota, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 180 days.

This patent is subject to a terminal disclaimer.

(21) Appl. No.: 13/877,403

(22) PCT Filed: Sep. 20, 2011

(86) PCT No.: PCT/JP2011/071318
§ 371 (c)(1),
(2), (4) Date: Apr. 2, 2013

(87) PCT Pub. No.: WO2012/046568
PCT Pub. Date: Apr. 12, 2012

(65) Prior Publication Data
US 2013/0190656 A1    Jul. 25, 2013

(30) Foreign Application Priority Data
Oct. 4, 2010  (JP) .................................. 2010-224709

(51) Int. Cl.
*A61B 5/00*  (2006.01)
*A61B 5/22*  (2006.01)
*G01L 19/14*  (2006.01)

(52) U.S. Cl.
CPC ............ *A61B 5/4205* (2013.01); *A61B 5/224* (2013.01); *A61B 5/4542* (2013.01); *A61B 5/682* (2013.01); *G01L 19/149* (2013.01)

(58) Field of Classification Search
CPC ........ A61B 5/038; A61B 5/228; A61B 5/4205; A61B 5/682; A61B 23/032;
(Continued)

(56) References Cited

U.S. PATENT DOCUMENTS 1,427,496 A * 8/1922 Ono ..................... A61B 5/1107
73/379.02
2,507,858 A * 5/1950 Kegel ........................... 600/591
(Continued)

FOREIGN PATENT DOCUMENTS

EP     1921432      5/2008
JP     2001-275994  10/2001
(Continued)

*Primary Examiner* — David J. McCrosky
(74) *Attorney, Agent, or Firm* — Hamre, Schumann, Mueller & Larson, P.C.

(57) ABSTRACT

A device for measuring oral cavity pressure includes the following: a pressure measuring probe having a balloon made of an elastic material is supported by a balloon base; a communicating member having an inner bore that communicates with the inside of the balloon via the balloon base to transmit the air pressure in the balloon; and a pressure detecting unit that is connected to the rear end of the communicating member and detects the transmitted air pressure. The balloon includes a pressure receiving portion that forms a cavity and a balloon tubular portion that communicates with the inside of the pressure receiving portion, and the balloon is joined to the front end portion of the balloon base with the balloon tubular portion. The balloon base has a rib that protrudes outward along the outer circumferential direction of the front end portion on the balloon side.

19 Claims, 9 Drawing Sheets

(58) Field of Classification Search
CPC .......... A61B 2562/0247; A61B 5/4542; A61B 5/4552; G01L 19/149
USPC ................. 600/587, 590; 73/379.01–379.09; 482/11
See application file for complete search history.

(56) References Cited

U.S. PATENT DOCUMENTS

| | | | |
|---|---|---|---|
| 3,910,743 A * | 10/1975 | Farrell | 425/533 |
| 4,697,601 A * | 10/1987 | Durkee | A61B 5/228 600/590 |
| 5,381,799 A * | 1/1995 | Hamilton et al. | 600/590 |
| 5,609,161 A | 3/1997 | Tura et al. | |
| 6,702,765 B2 * | 3/2004 | Robbins | A61B 5/228 600/590 |
| 8,366,639 B2 * | 2/2013 | Toyota et al. | 600/587 |
| 2006/0079814 A1 * | 4/2006 | Barlow | A61B 5/038 600/590 |
| 2008/0183107 A1 * | 7/2008 | Miller | A61B 5/228 600/590 |
| 2009/0091066 A1 | 4/2009 | Sleva et al. | |
| 2010/0121224 A1 | 5/2010 | Toyota et al. | |
| 2010/0222706 A1 | 9/2010 | Miyahara et al. | |

FOREIGN PATENT DOCUMENTS

| | | | |
|---|---|---|---|
| JP | 2006-204940 | 8/2006 | |
| JP | 2007-090054 | 4/2007 | |
| JP | 2008-237366 | 10/2008 | |
| JP | WO 2008117574 A1 * | 10/2008 | ............. A61B 5/038 |
| WO | WO 2007/026488 | 3/2007 | |

\* cited by examiner

| Compression angle | 0° (standard) | 15° | 30° |
|---|---|---|---|
| Conceptual diagram of balloon | | | |

| Compression angle | 45° | 60° | 90° |
|---|---|---|---|
| Conceptual diagram of balloon | | | |

FIG. 8

| Compression angle | 0° (standard) | | 15° | | 30° | | 45° | | 60° | | 90° | |
|---|---|---|---|---|---|---|---|---|---|---|---|---|
| | Ave. | ±3σ | Ave. | ±3σ | Ave. | ±3σ | Ave. | ±3σ | Ave. | ±3σ | Ave. | ±3σ |
| Applied load (N) 5 | 6.7 | 0.50 | 6.7 | 0.50 | 6.7 | 0.50 | 6.4 | 0.78 | *6.0* | 0.42 | *5.6* | 0.50 |
| 10 | 14.7 | 0.33 | 14.6 | 0.54 | 14.7 | 0.50 | 14.6 | 0.66 | *14.1* | 0.68 | *14.0* | 0.68 |
| 15 | 22.7 | 0.68 | 22.9 | 0.33 | 22.9 | 0.33 | 22.9 | 1.44 | 22.5 | 0.68 | 22.7 | 1.41 |
| 20 | 30.6 | 1.59 | 31.0 | 0.68 | 30.8 | 0.95 | 30.9 | 1.88 | 30.7 | 0.42 | 31.1 | 2.35 |
| 30 | 45.5 | 1.43 | 45.9 | 0.68 | 45.5 | 1.41 | 46.0 | 2.02 | 46.1 | 0.80 | 46.6 | 2.64 |
| 40 | 58.4 | 1.09 | 58.5 | 1.17 | 58.2 | 1.62 | 59.2 | 1.73 | 59.8 | 1.82 | 60.3 | 2.52 |
| 50 | 70.0 | 1.00 | 70.3 | 1.64 | 70.3 | 2.57 | 71.4 | 2.59 | 71.7 | 1.34 | 71.5 | 3.44 |
| 60 | 80.3 | 1.07 | 79.9 | 1.23 | 80.4 | 2.42 | 80.7 | 3.06 | *78.7* | 6.74 | *77.5* | 6.28 |

Maximum pressure (kPa)

DEVICE FOR MEASURING ORAL CAVITY PRESSURE, PRESSURE MEASURING PROBE

TECHNICAL FIELD

The present invention relates to a device for measuring oral cavity pressure that is used to measure oral cavity pressure such as tongue pressure, pressure of the hypoglossal muscle, lip pressure, or cheek pressure, and a pressure measuring probe that is used in the device.

BACKGROUND ART

A measurement using a device for measuring oral cavity pressure is performed in order to make a diagnosis of the function of the tongue, hypoglossal muscles, lips, cheeks, or the like. Such a diagnosis is carried out to analyze the feeding and swallowing function as part of the treatment for maintenance and restoration of the feeding and swallowing function of elderly people. The movement of the tongue is closely related to feeding and swallowing, and tongue pressure is required to form a bolus and force it into the pharynx. Therefore, the measurement and analysis of the tongue pressure have great significance. It is also important to measure other oral cavity pressure such as pressure of the hypoglossal muscle, lip pressure, or cheek pressure for an appropriate diagnosis.

FIG. 10 shows the configuration of a device for measuring oral cavity pressure of a conventional example, which is disclosed in Patent Document 1. This example uses a pressure measuring probe that includes a balloon as a pressing portion. When the balloon is inserted into the oral cavity and pressed by the tongue, the air pressure is detected and converted into an electrical signal by a transducer communicating with the balloon, so that the results of the measurement of the oral cavity pressure can be obtained.

The device for measuring oral cavity pressure shown in FIG. 10 functions with a pressure measuring probe 20 connected to a main body tube 22 of a main body device 21. The main body tube 22 is moderately thick and flexible to transmit the air pressure and is connected to a pressure detecting unit 24 via a valve 23. The pressure detecting unit 24 includes a pressure transducer that converts the air pressure into an electrical signal, and the output of the pressure transducer is supplied to a display unit 25 including, e.g., a digital panel. A pressurizing unit 26 is connected between the main body tube 22 and the pressure detecting unit 24 via the valve 23.

The pressure measuring probe 20 includes a rubber balloon 27, and the balloon 27 is connected to a probe tube 29 made of a hard plastic using a clamp ring 28. The balloon 27 is hermetically secured to the probe tube 29 with the clamp ring 28. A hard ring 30 is mounted on the balloon 27 between the attachment portion to the probe tube 29 and the inflatable portion.

The probe tube 29 has a male fitting portion 31, and the main body tube 22 has a female fitting portion 32. The probe tube 29 and the main body tube 22 are connected by fitting the male fitting portion 31 and the female fitting portion 32 together. The male fitting portion 31 and the female fitting portion 32 are luer taper fittings and are detachably fitted together. Therefore, the pressure measuring probe 20 is detachably connected to the main body device 21. Thus, if the part of the pressure measuring probe 20 is separately packaged and sterilized, only this part can be thrown away and replaced with a new one every time the tongue pressure or the like is measured. Consequently, the portion that is put in the mouth can always be kept clean and hygienic.

The hard ring 30 mounted on the balloon 27 has two functions. The first function is to prevent the base of the balloon 27 from being unnecessarily pressed by the incisors or the like so as to avoid an adverse effect on the pressure measurement. The second function is to perform positioning so that the hard ring 30 is positioned with respect to the lips or teeth when the balloon 27 is placed in the oral cavity, thereby enabling a stable pressure measurement.

In the measurement of the oral cavity pressure, first, the valve 23 is opened and pressure is applied until the pressure in the balloon 27 reaches a predetermined level. Next, the pressurized balloon 27 is placed in the mouth and pressed by the tongue to measure the maximum tongue pressure, the tongue pressure during swallowing, or the like. The pressure in the balloon 27 is adjusted, e.g., to about 10 to 30 kPa.

When the oral cavity pressure is measured, as shown in FIG. 11, the balloon 27 is held in the mouth with the hard ring 30 located at the position corresponding to the lips or the teeth 33. In this state, the balloon 27 is pressed by the tongue 34 at the maximum pressure, and thus the maximum tongue pressure can be measured. On the other hand, the balloon 27 is held in the mouth while a liquid is kept in the mouth, and changes in pressure with the swallowing movement are continuously monitored, so that the tongue pressure during swallowing can be measured. Accordingly, the function of the tongue of a patient can be analyzed by measuring the pressure exerted by various movements.

The pressure measuring probe 20 disclosed in Patent Document 1 is produced, e.g., in the form of a pressure measuring probe 20a shown in FIG. 12 as a real product. In FIG. 12, the components that are substantially the same as those of the configuration in FIG. 10 are denoted by the same reference numerals, and the explanation will not be repeated. As shown in FIG. 12, the pressure measuring probe 20a further includes the female fitting portion 32.

The pressure measuring probe 20a is produced by preparing each of the components shown in FIG. 12 and joining them together to form a structure of the pressure measuring probe 20a. In the pressure measuring probe 20a, the hard ring 30, the clamp ring 28, the probe tube 29, and the female fitting portion 32 are used as components to hold the balloon 27. As shown in FIG. 13, the balloon 27 includes a pressure receiving portion 27a that forms a cavity and a balloon tubular portion 27b that communicates with the inside of the pressure receiving portion 27a. The balloon 27 is connected to the probe tube 29 with the balloon tubular portion 27b.

PRIOR ART DOCUMENTS

Patent Documents

Patent Document 1: JP 2001-275994 A

DISCLOSURE OF INVENTION

Problem to be Solved by the Invention

However, the pressure measuring probe 20 disclosed in Patent Document 1 still has room for improvement, as described below, to ensure stable measurement accuracy.

In order to perform a stable measurement with high accuracy, when the balloon 27 is inserted into the oral cavity as shown in FIG. 11, the balloon 27 needs to be placed within an appropriate range in the longitudinal direction with respect to the tongue. This is because it is desirable for the central portion of the balloon 27 to be pressed when the balloon 27 is compressed by the tongue. In contrast, if the balloon 27 is located on the tongue at a shallow depth in the oral cavity, the end portion of the balloon 27 is pressed, and thus good measurement accuracy is not likely to be achieved.

However, the structure shown in FIG. 12 does not have the function of adjusting the position of the balloon 27 in the longitudinal direction of the tongue. Therefore, it is difficult to adjust the location of the balloon 27 appropriately so that good measurement accuracy can be stably achieved.

With the foregoing in mind, it is an object of the present invention to provide a device for measuring oral cavity pressure that uses a pressure measuring probe including a flat balloon and allows the balloon to be inserted into the oral cavity in an appropriate state, and that can stably ensure good measurement accuracy.

Means for Solving Problem

A device for measuring oral cavity pressure includes the following: a pressure measuring probe having a configuration in which a balloon made of an elastic material is supported by a balloon base; a communicating member having an inner bore that communicates with an inside of the balloon via the balloon base to transmit an air pressure in the balloon; and a pressure detecting unit that is connected to a rear end of the communicating member and detects the transmitted air pressure. The balloon includes a pressure receiving portion that forms a cavity and a balloon tubular portion that communicates with an inside of the pressure receiving portion, and the balloon is joined to a front end portion of the balloon base with the balloon tubular portion. To solve the above problem, the balloon base has a rib that protrudes outward along an outer circumferential direction of the front end portion on the balloon side.

A pressure measuring probe of the present invention includes a balloon that is made of an elastic material, and a balloon base that supports the balloon. The balloon includes a pressure receiving portion that forms a cavity and a balloon tubular portion that communicates with an inside of the pressure receiving portion, and the balloon is joined to a front end portion of the balloon base with the balloon tubular portion. To solve the above problem, the balloon base has a rib that protrudes outward along an outer circumferential direction of the front end portion on the balloon side.

Effects of the Invention

According to the above configurations, when the balloon is inserted into the oral cavity, the rib provided on the balloon base can facilitate the positioning of the balloon in the oral cavity. By bringing the rib into contact with the teeth, it is possible to prevent the position of the balloon from being too shallow in the oral cavity, and also to compress an appropriate position of the balloon. Thus, good measurement accuracy can be achieved.

BRIEF DESCRIPTION OF DRAWINGS

FIG. 8 is a front view showing the aspects of balloons of test samples used in the pressure response test.

FIG. 9 is a table showing the results of the pressure response test.

DESCRIPTION OF THE INVENTION

Figure 1:
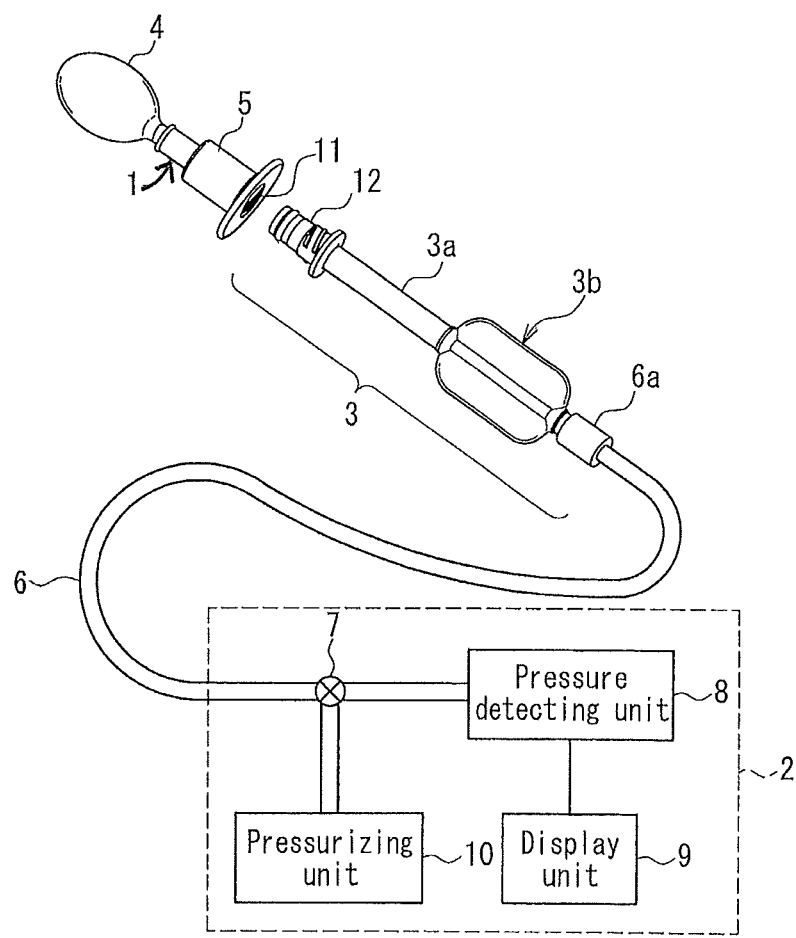
FIG. 1 is a perspective view showing the schematic configuration of a device for measuring oral cavity pressure of an embodiment of the present invention.

The device for measuring oral cavity pressure of the present invention can have the following aspects on the basis of the above configurations.

It is preferable that the communicating member includes a probe mounting member, in which the balloon base is detachably connected to a front end portion of the probe mounting member and a holding portion is provided in a rear of the probe mounting member, and a connecting tube that connects a rear end of the probe mounting member to the pressure detecting unit. With this configuration, the balloon is supported by one component, i.e., the balloon base, and the pressure measuring probe is separated from the probe mounting member. Therefore, the pressure measuring probe has a simple structure and can be produced at a low cost.

Moreover, a probe connecter may be provided at a rear end of the balloon base, and a mounting portion connector that can be detachably connected to the probe connector may be provided at the front end portion of the probe mounting member, so that the pressure measuring probe can be detachably connected to a main body side including the pressure detecting unit. With this configuration, since only the pressure measuring probe can be packaged and sterilized, it is easy to replace this portion with a new one every time the tongue pressure is measured.

It is preferable that an outer shape of a transverse section of the pressure receiving portion of the balloon that is perpendicular to an axial direction of the balloon tubular portion is a flat shape having a major axis and a minor axis, that the probe mounting member has an angle indicating portion that allows a specific direction of a rotation angle around an axis of the inner bore to be recognized, and that when the balloon base and the probe mounting member are being connected, an angle between the major axis of the flat shape of the balloon and the direction of the rotation angle indicated by the angle indicating portion is within a predetermined range. With this configuration, the angle between the major axis of the flat shape of the balloon and the direction of the rotation angle indicated by the angle indicating portion of the probe mounting member is controlled within the predetermined range. Thus, the balloon easily can be inserted into the oral cavity in an appropriate state, and good measurement accuracy can be ensured stably.

It is preferable that the holding portion is configured so as to be able to be held by the hand while touching the angle indicating portion and perform an operation of inserting the balloon into the oral cavity, and the direction of the rotation angle can be recognized by touching the angle indication portion with the hand. This configuration can eliminate the need for visual confirmation and improve the operability.

The holding portion may have a flat shape in which an outer shape extends in a direction of a plane containing an axial direction of the balloon tubular portion, and the holding portion may function as the angle indicating portion. By holding the holding portion, the holding portion is easily operable so that the rotation angle of the probe mounting member around the axis is constant.

It is preferable that the balloon base has a flange-like shielding portion with a large diameter at an end portion that is to be connected to the probe mounting member.

The presence of the shielding portion can prevent accidental swallowing of the pressure measuring probe during the measurement, even if the pressure measuring probe is made compact, and also can block the flow of saliva from the pressure measuring probe side to the probe mounting member side. Thus, the shielding portion also has the effect of keeping the probe mounting member clean and hygienic.

It is preferable that the balloon base is produced by insert molding in which an end portion of the balloon tubular portion is embedded, so that the balloon and the balloon base are joined to each other. The insert molding can provide a state in which the balloon and the balloon base are joined together. Thus, the balloon is secured without the use of an adhesive, and safety of the patient can be improved.

The pressure measuring probe of the present invention can have the following aspects on the basis of the above configurations.

It is preferable that a flange-like shielding portion with a large diameter is provided at an opening end of the balloon base. The presence of the shielding portion can prevent accidental swallowing of the pressure measuring probe during the measurement, even if the pressure measuring probe is made compact, and also can block the flow of saliva from the pressure measuring probe side to the probe mounting member side.

It is preferable that the balloon base is produced by insert molding in which an end portion of the balloon tubular portion is embedded, so that the balloon and the balloon base are joined to each other. The insert molding can provide a state in which the balloon and the balloon base are joined together. Thus, the balloon is secured without the use of an adhesive, and safety of the patient can be improved.

Hereinafter, a device for measuring oral cavity pressure of an embodiment of the present invention will be described in detail with reference to the drawings.

Embodiment

Figure 10:
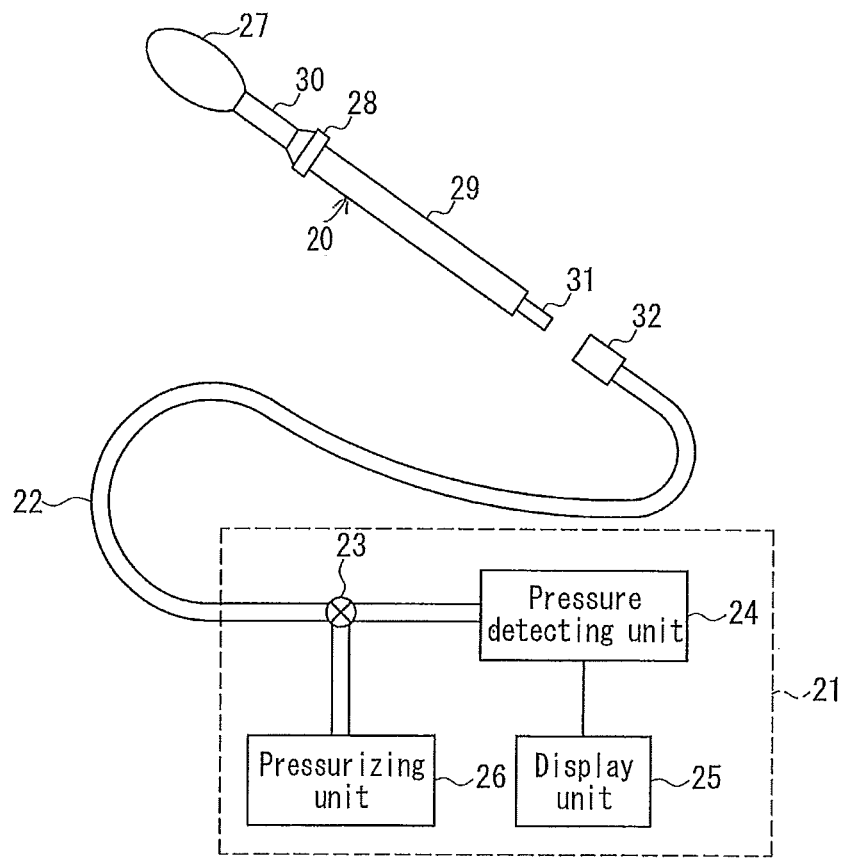
FIG. 10 is a front view showing the schematic configuration of a device for measuring oral cavity pressure of a conventional example.
Figure 11:
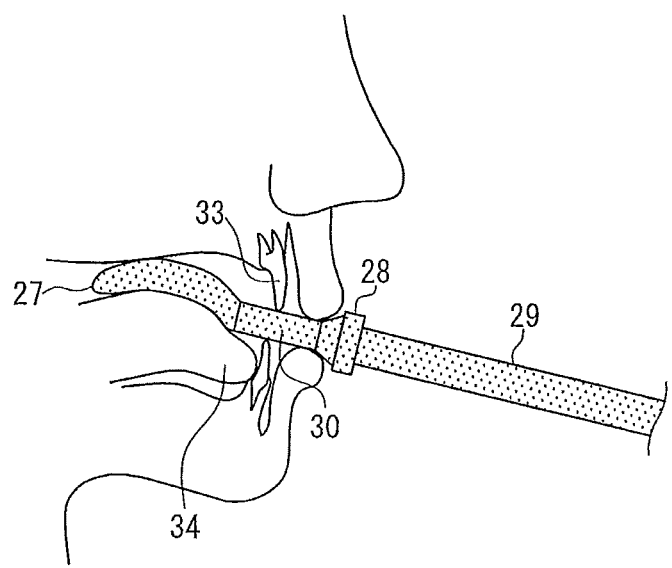
FIG. 11 is a cross-sectional view showing the use of a pressure measuring probe that constitutes a part of the device for measuring oral cavity pressure of the conventional example.

FIG. 1 is a perspective view showing the schematic configuration of a device for measuring oral cavity pressure of an embodiment of the present invention. The basic configuration of the device for measuring oral cavity pressure of this embodiment is the same as that of the conventional device shown in FIG. 10. First, this embodiment differs from the conventional example in the structure of a pressure measuring probe. Second, this embodiment also differs from the conventional example in the configuration of a communicating member (probe mounting member) that communicates with the inside of a balloon and transmits the air pressure in the balloon to a pressure detecting unit.

The device for measuring oral cavity pressure shown in FIG. 1 functions with a pressure measuring probe 1 connected to the front end portion of a probe mounting member 3 of a main body device 2. The pressure measuring probe 1 has a configuration in which a balloon 4 is supported by a balloon base 5. The opening end of the balloon base 5 can be detachably connected to the front end portion of the probe mounting member 3.

Figure 2:
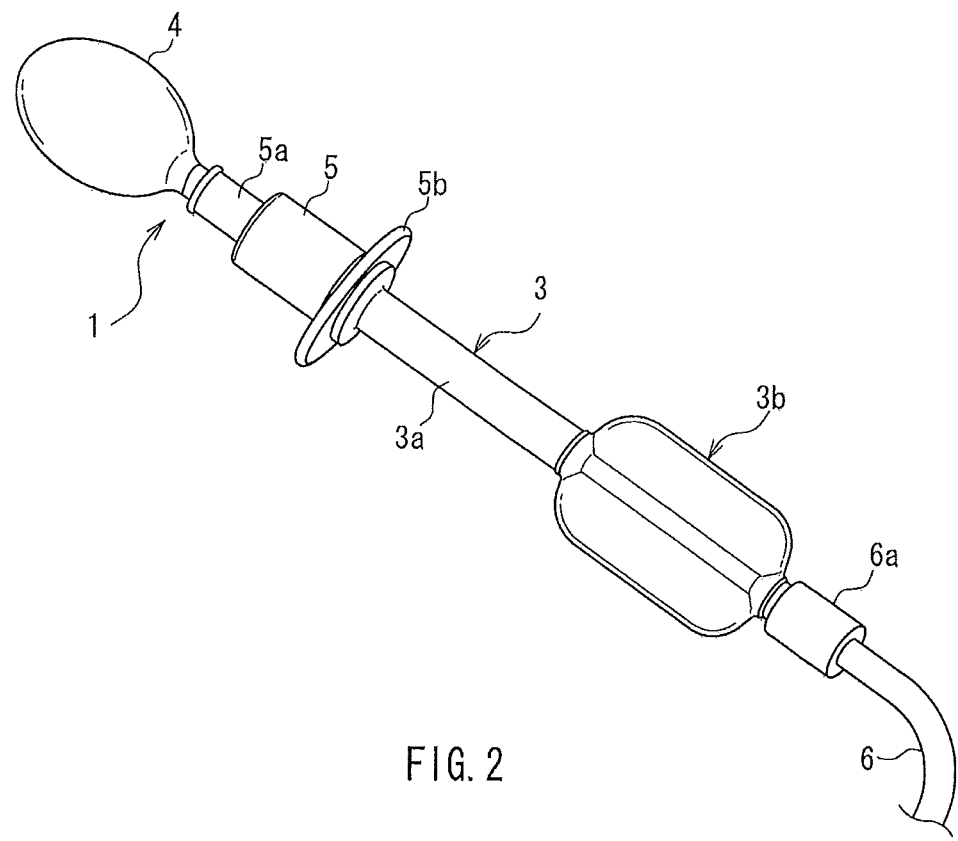
FIG. 2 is a perspective view showing a structure in which a pressure measuring probe and a holding portion are connected to form a measuring front portion of the device for measuring oral cavity pressure.

FIG. 2 shows a state in which the balloon base 5 is connected to the probe mounting member 3. With this connection, the pressure measuring probe 1 is mounted on the probe mounting member 3 to form a measuring front portion. When viewed from the whole structure of the device for measuring oral cavity pressure, the probe mounting member 3 constitutes a component that allows the pressure measuring probe 1 to be detachably mounted on the main body of the device for measuring oral cavity pressure.

As shown in FIG. 1, the rear end of the probe mounting member 3 is connected to the front end of a connecting tube 6 by a tube connector 6a. The connecting tube 6 is moderately thick and flexible to transmit the air pressure, and the rear end of the connecting tube 6 is connected to a pressure detecting unit 8 via a valve 7. The combined module of the probe mounting member 3 and the connecting tube 6 constitutes a communicating member that is attached to the main body device 2. The inner bore of the communicating member communicates with the inside of the balloon 4 so that the air pressure in the balloon 4 is transmitted to the pressure detecting unit 8.

The pressure detecting unit 8 includes a pressure transducer that converts the air pressure into an electrical signal, and the output of the pressure transducer is supplied to a display unit 9 including, e.g., a digital panel. A pressurizing unit 10 is connected between the connecting tube 6 and the pressure detecting unit 8 via the valve 7.

Figure 3A:
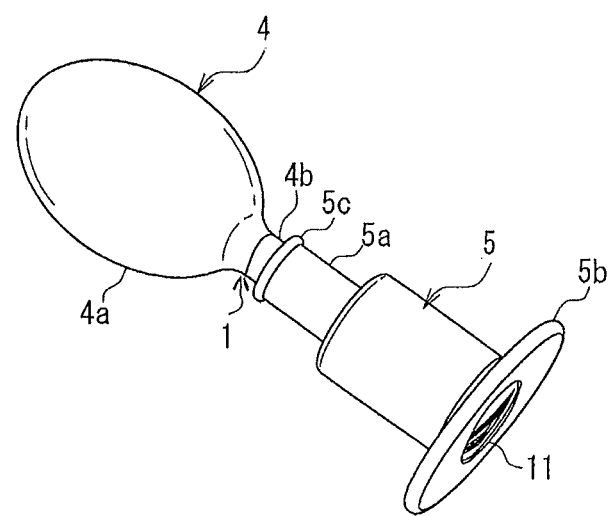
FIG. 3A is a perspective view of a pressure measuring probe used in the device for measuring oral cavity pressure.
Figure 3B:
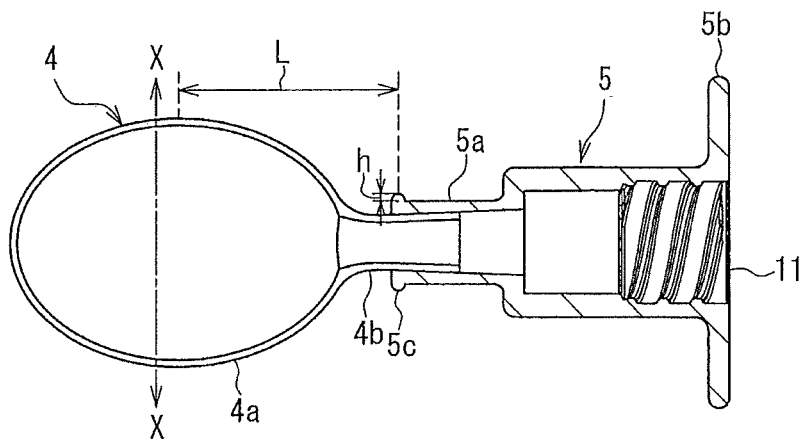
FIG. 3B is a longitudinal cross-sectional view of the pressure measuring probe shown in FIG. 3A.
Figure 3C:
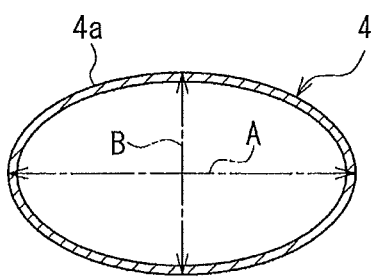
FIG. 3C is a transverse cross-sectional view of a balloon taken along the line X-X in FIG. 3B.

The structure of the pressure measuring probe 1 will be described with reference to FIGS. 3A to 3C. FIG. 3A is a perspective view of the pressure measuring probe 1. FIG. 3B is a longitudinal cross-sectional view of the pressure measuring probe 1. The balloon 4 is made of an elastic material and includes a pressure receiving portion 4a that forms a cavity and a balloon tubular portion 4b that communicates with the inside of the pressure receiving portion 4a. FIG. 3C shows a transverse sectional shape of the pressure receiving portion 4a. This transverse section of the pressure receiving portion 4a is a cross section taken along the line X-X in FIG. 3B, i.e., a cross section perpendicular to the axial direction of the balloon tubular portion 4b. As can be seen from FIG. 3C, the transverse section of the pressure receiving portion 4a has a flat shape with a major axis A direction and a minor axis B direction.

The balloon base 5 is made of a hard material, and the front end portion of balloon base 5 forms a balloon supporting portion 5a and is connected to the balloon tubular portion 4b. The rear end portion of the balloon base 5 is provided with a flange-like shielding portion 5b having a large diameter. A probe connector 11 having a female thread is, e.g., provided at the opening end of the inner bore of the balloon base 5 on the rear side. Moreover, a rib 5c that protrudes outward along the outer circumferential direction is provided at the front end (on the balloon 4 side) of the balloon supporting portion 5a.

The balloon base 5 is produced, e.g., from a hard resin material using insert molding in which the end portion of the balloon tubular portion 4b is embedded. The insert molding can provide a state in which the balloon 4 and the balloon base 5 are joined together. Thus, the balloon 4 is secured without the use of an adhesive, and safety of the patient can be improved.

Figure 4:
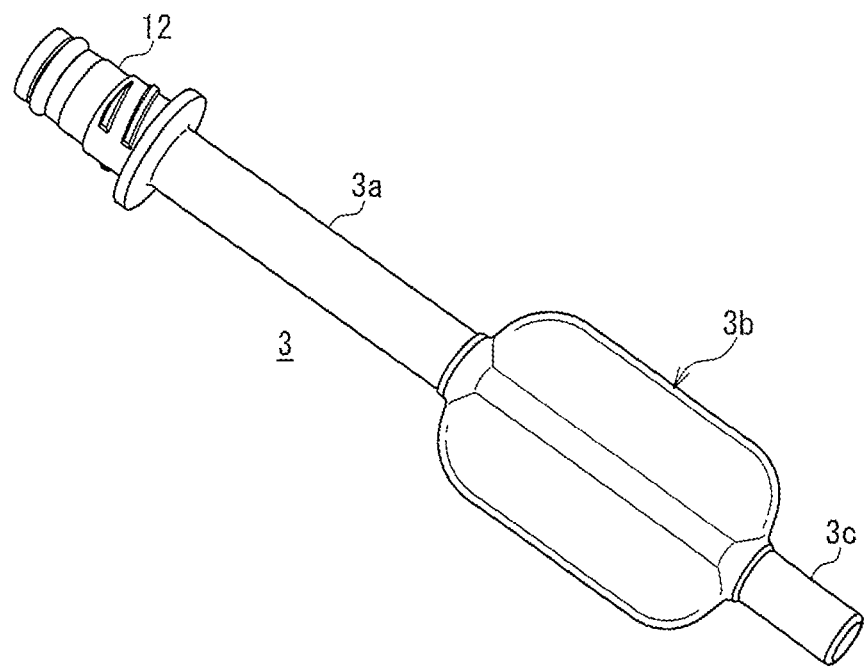
FIG. 4 is a perspective view showing a probe mounting member of the device for measuring oral cavity pressure.

As shown in FIG. 1, a tubular portion 3a having a circular cross section is formed in the middle of the probe mounting member 3. A mounting portion connector 12 is provided at the front end of the tubular portion 3a. A holding portion 3b is provided in the rear of the tubular portion 3a. The holding portion 3b is flat in shape and is to be held by the hand. FIG. 4 is a perspective view showing only the probe mounting member 3. As shown in FIG. 4, the mounting portion connector 12 has, e.g., a male thread that is to be screwed into the probe connector 11. Moreover, a tube coupling portion 3c is provided at the rear end of the probe mounting member 3 and coupled to the tube connector 6a (see FIGS. 1 and 2).

The holding portion 3b has a flat structure as a whole, and the flat structure has an outer shape that extends in the direction of the plane containing the tube axis of the tubular portion 3a. Needless to say, the mounting portion connector 12, the tubular portion 3a, the holding portion 3b, and the tube coupling portion 3c have inner bores that pass longitudinally through the probe mounting member 3.

With the connection between the probe connector 11 and the mounting portion connector 12, as shown in FIG. 2, the balloon base 5 and the probe mounting member 3 are detachably connected, thereby forming the measuring front portion. In this connected state, the holding portion 3b is held and operated by the hand so that the balloon 4 can be inserted into the oral cavity and the tongue pressure can be measured appropriately.

According to the above structure of the device for measuring oral cavity pressure, only the pressure measuring probe 1 can be packaged and sterilized, and this component need be replaced with a new one every time the tongue pressure is measured. Thus, the cleanliness of the portion that is put in the mouth can be maintained at all times. Moreover, the balloon base 5 supporting the balloon 4 has a simple structure that is formed solely of an integrated resin material.

Figure 12:
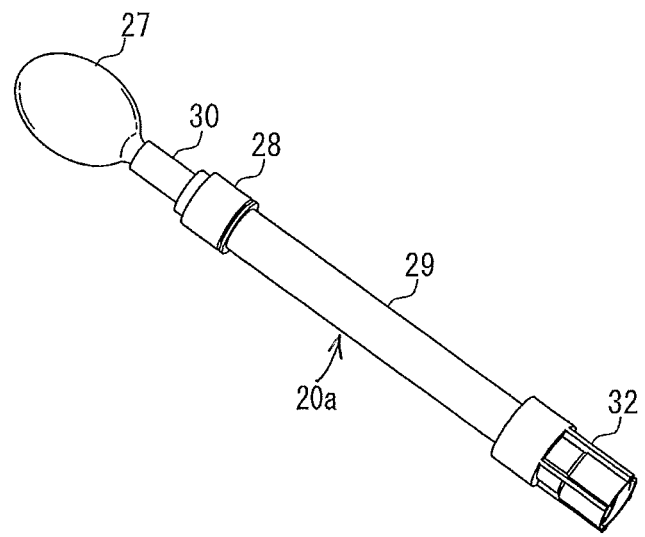
FIG. 12 is a perspective view showing the structure of a measuring front portion including the pressure measuring probe.
Figure 13:
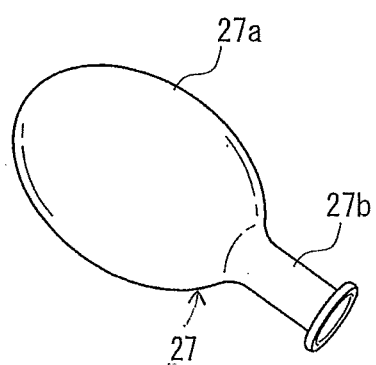
FIG. 13 is a perspective view of a balloon that is a component of the pressure measuring probe.

In the pressure measuring probe 1 of this embodiment, the balloon base 5 incorporates the hard ring 30 and the clamp ring 28 of the pressure measuring probe 20a of the conventional example shown in FIG. 12 as an integral component. Moreover, the probe tube 29 of the pressure measuring probe 20a corresponds to the probe mounting member 3 that is separated from the pressure measuring probe 1 and constitutes a part of the communicating member of the main body. Therefore, the pressure measuring probe 1 is extremely simple compared to the conventional example shown in FIG. 12, and thus can be inexpensive and easy to use as a disposable replacement component.

As a result of the above improvement of this embodiment, the pressure measuring probe 1 is made compact because it is composed only of the balloon 4 and the balloon base 5. Therefore, there is a fear that the pressure measuring probe 1 may be swallowed accidentally during the measurement. The shielding portion 5b at the rear end of the balloon supporting portion 5a is a component that has the function of preventing such accidental swallowing of the pressure measuring probe 1. Moreover, the presence of the shielding portion 5b also has the effect of blocking the flow of saliva from the pressure measuring probe 1 side to the probe mounting member 3 side.

On the other hand, the rib 5c provided on the balloon supporting portion 5a is a component that has the function of facilitating the positioning of the balloon 4 in the oral cavity by coming into contact with the teeth when the balloon 4 is inserted into the oral cavity. In order to achieve good measurement accuracy, the balloon 4 needs to be placed within an appropriate range in the longitudinal direction with respect to the tongue. This is because it is desirable for the central portion of the pressure receiving portion 4a of the balloon 4 to be pressed when the balloon 4 is compressed by the tongue. In contrast, if the balloon 4 is located on the tongue at a shallow depth in the oral cavity, the end portion of the pressure receiving portion 4a may be pressed, and thus good measurement accuracy is not likely to be achieved. Therefore, the use of the rib 5c to prevent the position of the balloon 4 from being too shallow in the oral cavity is effective in achieving good measurement accuracy.

Figure 3D:
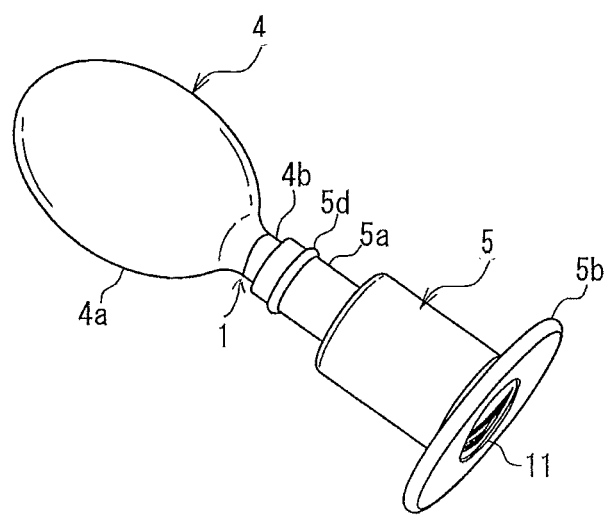
FIG. 3D is a perspective view showing another aspect of a pressure measuring probe used in the device for measuring oral cavity pressure.

In order to perform the positioning function sufficiently, it is desirable that the height h (see FIG. 3B) of the rib 5c protruding from the surface of the balloon supporting portion 5a is 0.2 to 5 mm. However, since the upper limit is appropriately in the range that will not interfere with the practical use, it does not substantially affect the positioning effect. The distance L between the center of the pressure receiving portion 4a of the balloon 4 and the rib 5c in the axial direction is preferably 10 to 25 mm. The position where the rib 5c is to be provided is not limited to the front end of the balloon supporting portion 5a, and, as shown in FIG. 3D, the rib 5d can also be located at a position that is slightly retracted from the front end. In short, the position of the rib 5c may be adjusted appropriately in accordance with, e.g., the structural relationship with the pressure receiving portion 4a of the balloon 4 or the balloon supporting portion 5a.

The drawings show that the rib 5c is formed continuously in the outer circumferential direction of the balloon supporting portion 5a. However, there may be a discontinuity in the shape of the rib 5c. In other words, the rib 5c may have any protruding shape as long as it can ensure the function of facilitating the positioning of the balloon 4 in the oral cavity by coming into contact with the teeth.

The above effect of the balloon supporting portion 5a due to the presence of the rib 5c is not limited to the configuration in which the pressure receiving portion 4a of the balloon 4 has a flat shape. Even if the pressure receiving portion 4a has other shapes such as a circular shape, the effect of being able to adjust the position of the balloon appropriately in the oral cavity can be obtained similarly. Moreover, the above effect of the rib 5c is also not limited to the configuration in which the pressure measuring probe 1 is mounted on the probe mounting member 3 having the holding portion 3b. Even if the balloon base 5 of the pressure measuring probe 1 is directly mounted on the connecting tube 6, the above effect can be obtained accordingly. Alternatively, even if the balloon base 5 is long enough to be held, the above effect can be obtained accordingly.

Figure 5:
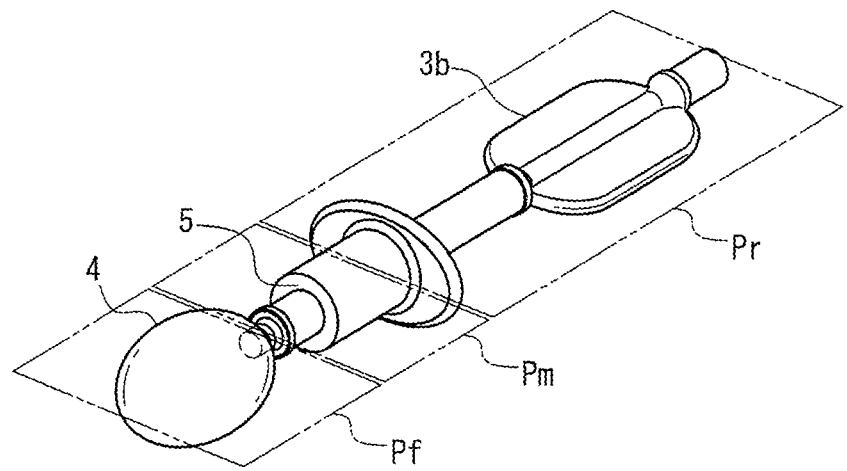
FIG. 5 is a perspective view for explaining the function and the effect in the configuration of the measuring front portion shown in FIG. 2.

Further, in this embodiment, the function obtained by using the flat holding portion 3b of the probe mounting member 3 will be described with reference to FIG. 5. In FIG. 5, a front plane Pf is a plane containing a direction of the major axis A of the pressure receiving portion 4a of the balloon 4. A rear plane Pr is a plane parallel to the planar direction of the holding portion 3b. A middle plane Pm is a particular plane parallel to the tube axis of the balloon base 5. That is, the middle plane Pm is a plane having a certain relationship with the posture of the balloon base 5.

As described above, the transverse sectional shape of the pressure receiving portion 4a of the balloon 4 is a flat shape having the major axis A and the minor axis B. This results in the effect of improving the linearity of the relationship between the applied load and the detected pressure so as to enhance the measurement accuracy. Moreover, compared to a circular transverse section, the pressure receiving portion 4a with the flat transverse section easily can be made stable in the oral cavity and also can be compressed by the tongue in a way that is not likely to vary from person to person, so that the measurement accuracy can be stabilized. However, to perform a stable measurement with high accuracy, it is desirable that when the balloon 4 is inserted into the oral cavity, the balloon 4 is placed on the tongue with the direction of the major axis A of the pressure receiving portion 4a, i.e., the front plane Pf, being parallel to the surface of the tongue.

For this purpose, in this embodiment, the mutual directional relationship of the pressure measuring probe 1 and the probe mounting member 3 have to be controlled. Since the balloon base 5 and the probe mounting member 3 are detachably connected, depending on the mounted state of the balloon base 5, the posture of the balloon 4 inserted into the oral cavity can change with the rotation angle around the axis. That is, the rotation angle of the major axis A of the pressure receiving portion 4a of the balloon 4 relative to the probe mounting member 3 is not necessarily constant without taking any measures.

When the balloon 4 is inserted into the oral cavity to measure the tongue pressure, a person to be measured holds and operates the probe mounting member 3. Therefore, the structure is adjusted such that when the person to be measured holds the holding portion 3b of the probe mounting member 3, the direction of the rotation angle of the probe mounting member 3 around the axis is constant, i.e., it is easy to operate the probe mounting member 3 so that the rear plane Pr is oriented in a specific direction.

Moreover, the connection structures of the probe connecter 11 and the mounting portion connector 12 are determined so that the correlation between the rotation angles of the probe connector 11 and the mounting portion connector 12 around their axes is maintained constant while they are connected to each other. Therefore, as a matter of course, the correlation between the rotation angles of the probe mounting member 3 and the balloon base 5 around their axes is also maintained constant while they are connected to each other. Thus, if the middle plane Pm is set parallel to the rear plane Pr, the rear plane Pr and the middle plane Pm are always parallel when the probe mounting member 3 and the balloon base 5 are being connected. In this embodiment, the probe connector 11 and the mounting portion connector 12 are formed of the female thread and the male thread, respectively, and the starting positions of the threads are fixed, thereby providing such a state. However, the connection structures for obtaining the similar effect are not limited thereto, and easily can be selected from known structures.

When the correlation between the rotation angles of the balloon base 5 and the major axis A of the balloon 4 around their axes is constant, i.e., when the middle plane Pm and the front plane Pf are always parallel, the front plane Pf and the rear plane Pr are parallel. In other words, the major axis A of the pressure receiving portion 4a becomes parallel to the planar direction of the holding portion 3b of the probe mounting member 3. Therefore, by holding and operating the probe mounting member 3, the probe mounting member 3 is easily operable so that the major axis A of the balloon 4 is parallel to the surface of the tongue when the balloon 4 is inserted into the oral cavity.

As will be described later, when the balloon base 5 is formed by insert molding in which the end portion of the balloon tubular portion 4b is embedded, it is difficult to make the correlation between the rotation angles of the two components around their axes constant, i.e., to make the middle plane Pm and the front plane Pf parallel stably. Therefore, it is desirable that a variation in angular relationship is adjusted to fall in the range that will not interfere with the practical use.

As described above, in order to control the correlation between the rotation angles of the pressure measuring probe 1 and the probe mounting member 3, the probe mounting member 3 needs to have an angle indicating portion that enables a person to be measured to recognize a specific direction of the rotation angle around the axis. The holding portion 3b is an example of the angle indicating portion, and it is possible to recognize the planar direction of the holding portion 3b as a specific direction of the rotation angle. Moreover, when the balloon base 5 and the probe mounting member 3 are being connected, the angle between the major axis A of the flat shape of the balloon 4 and the direction of the rotation angle indicated by the angle indicating portion is within a predetermined range.

It is desirable that the angle indicating portion is configured so that it is possible to recognize the direction of the rotation angle by touching the angle indicating portion with the hand. Therefore, when the person to be measured holds and operates the probe mounting member 3, the person to be measured can recognize the direction of the rotation angle of the probe mounting member 3 by touching the angle indicating portion, and thus can easily adjust the direction of the major axis A of the pressure receiving portion 4a. However, even if the angle indicating portion is configured, e.g., so that the direction of the rotation angle can be identified visually, the effect can be obtained accordingly.

Figure 6:
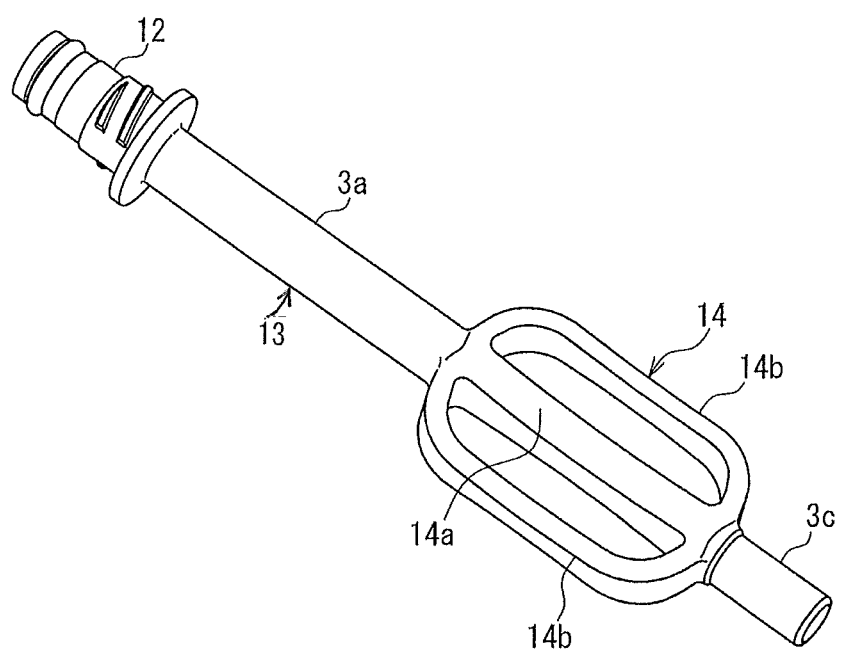
FIG. 6 is a perspective view showing another configuration of a probe mounting member of the device for measuring oral cavity pressure.

In order to obtain the above effect, the holding portion 3b of the probe mounting member 3 that serves as the angle indicating portion is not limited to a flat shape as described above, and may have various aspects. For example, the holding portion 3b also can have a configuration shown in FIG. 6. In FIG. 6, a holding portion 14 of a probe mounting member 13 is composed of an axial portion 14a and side branch portions 14b located on both sides of the axial portion 14a, and has a flat structure as a whole. The axial portion 14a has an inner bore that passes longitudinally through the probe mounting member 13. In addition to the above, the holding portion may also have, e.g., an elliptical, circular, or rectangular flat shape. The holding portion can be in any form as long as it is flat. Moreover, it is preferable that the thickness of the holding portion is the same as that of the tubular portion 3a because the holding portion can be held more easily.

Next, in the balloon base 5 formed by insert molding, the angle between the probe connector 11 and the plane containing the major axis A of the pressure receiving portion 4a, i.e., the angle between the middle plane Pm and the front plane Pf has been studied to determine the range in which practically sufficient measurement accuracy of the tongue pressure can be achieved, and the results will be described.

As described above, the dihedral angle between the balloon base 5 and the probe mounting member 3, i.e., the angle between the middle plane Pm and the rear plane Pr can be controlled in design terms, e.g., by appropriately setting the starting positions of the threads of the probe connector 11 and the mounting portion connector 12. However, the dihedral angle between the balloon 4 and the balloon base 5, i.e., the angle between the front plane Pf and the middle plane Pm is likely to deviate during the insert molding. Therefore, it is difficult to avoid such a deviation with the design. If the angular deviation is significant, the balloon 4 may not be compressed in an appropriate direction at the time of the measurement.

In order to examine the effect of the difference in the compression direction of the balloon 4 on the pressure responsibility of the device for measuring oral cavity pressure, a pressure response test was performed on various different compression directions (angles) to determine the tolerance for the deviation of the dihedral angle between the balloon 4 and the balloon base 5, i.e., the deviation of the angle between the balloon 4 and the holding portion 3b of the probe mounting member 3.

<Test Method>

Figure 7:
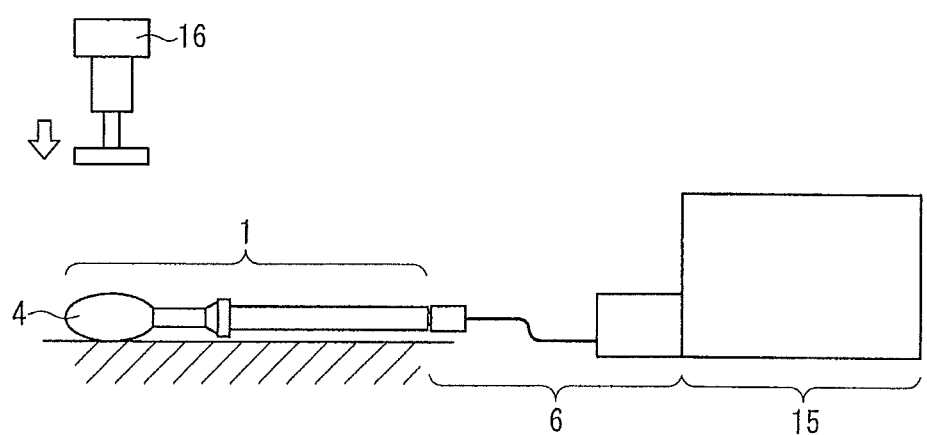
FIG. 7 is a front view showing a method of a pressure response test that is performed on different compression directions (angles) of a pressure measuring probe.

As shown in FIG. 7, the pressure measuring probe 1, the connecting tube 6, and a digital tongue manometer 15 were connected, and pressure was applied until the internal pressure of the balloon 4 reached 19.6 kPa. Next, the balloon 4 of the pressure measuring probe 1 was compressed while controlling the load by a tensile tester 16, and the maximum pressure displayed on the digital tongue manometer 15 for each load was recorded.

Eight different loads of 5, 10, 15, 20, 30, 40, 50, and 60 N were applied. The number of test samples n was five. The rate of compression was 20 mm/min. FIG. 8 shows the aspects of the balloons of each of the test samples. The compression direction was the vertical direction with respect to the pressure receiving portion of each of the balloons represented by the "conceptual diagrams of balloons". In the "conceptual diagrams of balloons", the major axis A of the pressure receiving portion is illustrated. The compression angle is an angle between the major axis A of the pressure receiving portion of each of the balloons and the horizontal direction.

<Test Results>

FIG. 9 is a table showing the data of the test results. In the table, Ave. of the maximum pressure data is the average of the number of the test samples (n=5) and $\pm 3\sigma$ is a variation in the data. The numeric data in FIG. 9 have the following three tendencies as the compression angle increases.

(1) The variation in the data ($\pm 3\sigma$) is increased (the data in the regions indicated by high-density dots in the table).

(2) There are regions where the average is likely to be reduced (the italic data in the regions indicated by low-density dots in the table).

(3) There are regions where the average is likely to be increased (the data in the regions indicated by low-density dots in the table).

As described above, it is evident that the compression angle of the balloon affects the performance of the device for measuring oral cavity pressure, i.e., the measurement accuracy and the pressure responsibility. To deal with this issue, it is desirable that the tolerance for the deviation of the dihedral angle between the balloon 4 and the balloon base 5 should be set.

<Setting of Tolerance for Angle Deviation Based on Test Results>

Based on the results shown in the table of FIG. 9, $\pm 3\sigma$ was evaluated as a variation in the average of the maximum pressure displayed for each load. The evaluation criterion was that "a variation ($\pm 3\sigma$) in the average of the maximum pressure is within 2 kPa". Consequently, it was confirmed that the deviation of the dihedral angle between the balloon 4 and the balloon base 5 was preferably 15° or less to meet the above criterion. In order to obtain the results of the measurement with high accuracy, it is desirable that the angle between the major axis of the flat shape of the balloon 4 and the direction of the rotation angle indicated by the holding portion 3b (angle indicating portion) of the probe mounting member 3 is in the range of 0 to 15 degrees.

Even if the tolerance conditions are not satisfied, appropriate measurement results can be obtained depending on the practical circumstances.

For the above device for measuring oral cavity pressure of this embodiment, the material of the balloon 4 is preferably an elastic material such as natural rubber, synthetic rubber, or silicone rubber. However, a flexible material such as a flexible plastic can also be used. In the case of the elastic material, the balloon 4 may be produced by the same forming technique as that used for a medical balloon or a balloon. In the case of the flexible material, the balloon 4 can be produced by forming a film into a bag.

The material of the balloon base 5 is preferably a hard material because it is easily held when the balloon 4 is put in the mouth. In particular, a hard plastic such as polypropylene, polyethylene, or polycarbonate is preferred. The connecting tube 6 preferably is made of a flexible plastic such as flexible polyvinyl chloride, polybutadiene, flexible polypropylene, flexible polyethylene, or ethylene-vinyl acetate copolymer in terms of the operability. However, it is difficult to perform an accurate pressure measurement if the connecting tube 6 is too flexible and thin. Therefore, the tube with moderate flexibility and thickness is preferred.

The pressure detecting unit 8 is configured so as to convert the air pressure into an electrical signal, e.g., using a pressure inlet type strain gauge pressure transducer. The pressure detecting unit 8 may include an amplifier for amplifying the signal before outputting it to the display unit 9. Any other types of pressure transducers may also be used. The valve 7 is not essential depending on the structure of the pressurizing unit 10, and the pressurizing unit 10 can be connected directly to the connecting tube 6.

In the above embodiment, the measurement of the tongue pressure has been described. However, the same configuration can be used to measure the oral cavity pressure such as the pressure of the hypoglossal muscle, the lip pressure, or the cheek pressure. In such a case, it is desirable that the size of the balloon, the thickness and shape of the tube, or the like is modified to be appropriate for the intended purpose.

INDUSTRIAL APPLICABILITY

According to the device for measuring oral cavity pressure of the present invention, a balloon can be inserted easily into the oral cavity in an appropriate state, and good measurement accuracy can be stably ensured. Therefore, the device for measuring oral cavity pressure is useful as a device for measuring the tongue pressure, the pressure of the hypoglossal muscle, the lip pressure, the cheek pressure, or the like.

DESCRIPTION OF REFERENCE NUMERALS 1, 20, 20a Pressure measuring probe
2, 21 Main body device
3, 13 Probe mounting member
3a Tubular portion
3b, 14 Holding portion
3c Tube coupling portion
4, 27 Balloon
4a, 27a Pressure receiving portion
4b, 27h Balloon tubular portion
5 Balloon base
5a Balloon supporting portion
5b Shielding portion
5c, 5d Rib
6 Connecting tube
6a Tube connector
7, 23 Valve
8, 24 Pressure detecting unit
9, 25 Display unit
10, 26 Pressurizing unit
11 Probe connector
12 Mounting portion connector
14a Axial portion
14b Side branch portion
22 Main body tube
28 Clamp ring
29 Probe tube
30 Hard ring
31 Male fitting portion
32 Female fitting portion
33 Teeth
34 Tongue
A Major axis
B Minor axis
Pf Front plane
Pm Middle plane
Pr Rear plane

The invention claimed is:

1. A device for measuring oral cavity pressure comprising:
a pressure measuring probe having a balloon made of an elastic material, the balloon being supported by a balloon supporting portion of a balloon base;
a connecting tube having an inner bore that communicates with an inside of the balloon via an inner bore in the balloon base that communicates with the inside of the balloon to transmit an air pressure in the balloon; and
a pressure detecting unit that detects the transmitted air pressure via the connecting tube,
wherein the balloon includes a pressure receiving portion that forms a cavity and a balloon tubular portion that communicates with an inside of the pressure receiving portion, and the balloon is joined to a front end portion of the balloon supporting portion via the balloon tubular portion of the balloon,
wherein the balloon supporting portion has an upright rib that protrudes from an outer circumferential surface of the front end portion on a balloon side,
wherein the pressure receiving portion has a flat cross-sectional shape, the flat cross-sectional shape having a major axis and a minor axis shorter than the major axis,
wherein the balloon tubular portion has a first end connected to the pressure receiving portion, and a second end that extends past the rib, and
wherein the device is configured so that the rib contacts teeth such that the balloon is in a position where a central portion of the pressure receiving portion of the balloon is pressed by a tongue when the balloon is inserted into an oral cavity and the outer circumferential surface of the front end portion is held by the teeth.

2. The device for measuring oral cavity pressure according to claim 1, wherein the balloon base is produced by insert molding in which an end portion of the balloon tubular portion is embedded, so that the balloon and the balloon base are joined to each other.

3. The device for measuring oral cavity pressure according to claim 1, wherein the device includes a probe mounting member, the balloon base has a connecting portion on a rear side and the probe mounting member has a front end portion so that the connecting portion of the balloon base is connected to the front end portion of the probe mounting member, and
wherein a diameter of the connecting portion is larger than that of the balloon supporting portion so that a step is formed.

4. The device for measuring oral cavity pressure according to claim 3, wherein the front end portion of the probe mounting member is detachably connected to the connecting portion of the balloon base.

5. The device for measuring oral cavity pressure according to claim 4, wherein the connecting portion of the balloon base is a probe connector provided at a rear end portion of the balloon base, and the front end portion of the probe mounting member is a mounting portion connector that is detachably connected to the probe connector, so that the pressure measuring probe is detachably connected to a main body side including the pressure detecting unit.

6. The device for measuring oral cavity pressure according to claim 4, wherein
the probe mounting member has an angle indicating portion that allows a specific direction of a rotation angle around an axis of the inner bore to be recognized, and
when the balloon base and the probe mounting member are being connected, an angle between the major axis direction of the flat shape of the balloon and the direction of the rotation angle indicated by the angle indicating portion is within a predetermined range.

7. The device for measuring oral cavity pressure according to claim 6, wherein the holding portion is held by the hand while touching the angle indicating portion so as to be able to perform an operation of inserting the balloon into the oral cavity, and the direction of the rotation angle is recognized by touching the angle indicating portion with the hand.

8. The device for measuring oral cavity pressure according to claim 6, wherein the holding portion has a flat shape in which an outer shape extends in a direction of a plane containing an axial direction of the balloon tubular portion, and the holding portion functions as the angle indicating portion.

9. The device for measuring oral cavity pressure according to claim 4, wherein the balloon base has a flange-like shielding portion with a large diameter at an end portion.

10. The device for measuring oral cavity pressure of claim 1, wherein a distance between the rib and a center of the pressure receiving portion is between 10 mm and 25 mm.

11. The device for measuring oral cavity pressure of claim 1, wherein the rib is formed continuously in the outer circumferential surface of the balloon supporting portion.

12. A pressure measuring probe comprising:
a balloon that is made of an elastic material; and
a balloon base that supports the balloon at a balloon supporting portion of the balloon base,
wherein a rear end portion of the balloon base is configured to connect to a pressure detecting unit so as to detect air pressure in the balloon,
wherein the balloon includes a pressure receiving portion that forms a cavity and a balloon tubular portion that communicates with an inside of the pressure receiving portion, and the balloon is joined to a front end portion of the balloon supporting portion via the balloon tubular portion of the balloon,
wherein the balloon supporting portion has an upright rib that protrudes from an outer circumferential surface of the front end portion, and
wherein the balloon tubular portion has a first end connected to the pressure receiving portion, and a second end that extends past the rib,
wherein the pressure receiving portion has a flat cross-sectional shape, the flat cross-sectional shape having a major axis and a minor axis shorter than the major axis,
wherein the pressure measuring probe is configured so that the rib contacts teeth such that the balloon is in a position where a central portion of the pressure receiving portion of the balloon is pressed by a tongue when the balloon is inserted into an oral cavity and the outer circumferential surface of the front end portion is held by the teeth, and
wherein the balloon base comprises an inner bore in communication with an inside of the balloon to transmit an air pressure in the balloon.

13. The pressure measuring probe according to claim 12, wherein the balloon base is produced by insert molding in which an end portion of the balloon tubular portion is embedded, so that the balloon and the balloon base are joined to each other.

14. The pressure measuring probe according to claim 12, wherein the pressure measuring probe includes a probe mounting member, and the balloon base has a connecting portion on a rear side so as to be connected to a front end portion of the probe mounting member.

15. The pressure measuring probe according to claim 14, wherein the balloon base has a flange-like shielding portion with a large diameter at an end portion.

16. The pressure measuring probe of claim 12, wherein a distance between the rib and a center of the pressure receiving portion is between 10 mm and 25 mm.

17. The pressure measuring probe of claim 12, wherein the rib is formed continuously in the outer circumferential surface of the balloon supporting portion.

18. A device for measuring oral cavity pressure comprising:
a balloon that is made of an elastic material;
a tubular member that supports the balloon at a front end and has an inner bore that communicates with an inside of the balloon to transmit an air pressure in the balloon; and
a pressure detecting unit that is connected to a rear end of the tubular member via a connecting tube and detects the transmitted air pressure,
wherein the balloon includes a pressure receiving portion that forms a cavity and a balloon tubular portion that communicates with an inside of the pressure receiving portion, and the balloon is joined to a front end portion of the tubular member with the balloon tubular portion,
wherein the pressure receiving portion has a flat cross-sectional shape, the flat cross-sectional shape having a major axis and a minor axis, the minor axis shorter than the major axis,
wherein the tubular member is divided into a balloon base to which the balloon tubular portion is joined, and a probe mounting member to a front end of which the balloon base is detachably connected, in which the probe mounting member is provided with a holding portion at a rear portion, the balloon and the balloon base joined to each other composing a pressure measuring probe that is detachably connected to the probe mounting member,
wherein the balloon base has a rib that protrudes outward along an outer circumferential direction of a front end portion on the balloon side, and the device is configured so that the rib contacts teeth such that the balloon is in a position where a central portion of the pressure receiving portion of the balloon is pressed by a tongue when the balloon is inserted into an oral cavity and the front end portion of the balloon base is held by the teeth.

19. A pressure measuring probe comprising:
a balloon that is made of an elastic material; and
a tubular member that supports the balloon at a front end and has an inner bore that communicates with an inside of the balloon to transmit an air pressure in the balloon,
wherein the balloon includes a pressure receiving portion that forms a cavity and a balloon tubular portion that communicates with an inside of the pressure receiving portion, and the balloon is joined to a front end portion of the tubular member with the balloon tubular portion,
thereby configured to be capable of detecting the air pressure in the balloon when connecting a rear end of the tubular member to a pressure detecting unit,
wherein the pressure receiving portion has a flat cross-sectional shape, the flat cross sectional shape having a major axis and a minor axis, the minor axis shorter than the major axis,
wherein the tubular member is divided into a balloon base on a front side to which the balloon tubular portion is joined, and a probe mounting member on a rear side, at which a holding portion is provided, the balloon and the balloon base joined to each other composing the pressure measuring probe,
wherein a rear end portion of the balloon base can be detachably connected to the probe mounting member that is connected to the pressure detecting unit, and
wherein the balloon base has a rib that protrudes outward along an outer circumferential direction of a front end portion on the balloon side, and the pressure measuring probe is configured so that the rib contacts teeth such that the balloon is in a position where a central portion of the pressure receiving portion of the balloon is pressed by a tongue when the balloon is inserted into an oral cavity and the front end portion of the balloon base is held by the teeth.

* * * * *